(12) United States Patent
Boschetti et al.

(10) Patent No.: US 7,326,776 B2
(45) Date of Patent: Feb. 5, 2008

(54) PREPARATION AND USE OF MIXED MODE SOLID SUBSTRATES FOR CHROMATOGRAPHY ADSORBENTS AND BIOCHIP ARRAYS

(75) Inventors: Egisto Boschetti, Croissy sur Sein (FR); Pierre Girot, Paris (FR)

(73) Assignee: Pall Corporation, East Hills, NY (US)

( * ) Notice: Subject to any disclaimer, the term of this patent is extended or adjusted under 35 U.S.C. 154(b) by 0 days.

(21) Appl. No.: 11/531,863

(22) Filed: Sep. 14, 2006

(65) Prior Publication Data

US 2007/0015143 A1 Jan. 18, 2007

Related U.S. Application Data

(62) Division of application No. 10/660,738, filed on Sep. 12, 2003, now Pat. No. 7,144,743.

(60) Provisional application No. 60/410,273, filed on Sep. 13, 2002.

(51) Int. Cl.
*C07K 1/22* (2006.01)
*G01N 33/53* (2006.01)
*C12M 1/34* (2006.01)

(52) U.S. Cl. .................. 530/415; 530/404; 530/405; 530/812; 435/287.1; 435/7.8; 435/7.92

(58) Field of Classification Search .............. 530/415, 530/404, 405, 812; 435/287.1, 7.8, 7.92
See application file for complete search history.

(56) References Cited

U.S. PATENT DOCUMENTS

| | | | |
|---|---|---|---|
| 3,305,362 A | 2/1967 | Riester et al. | |
| 4,381,239 A | 4/1983 | Chibata et al. | |
| 4,696,980 A | 9/1987 | Porath | |
| 4,701,500 A | 10/1987 | Porath | |
| 5,075,371 A | 12/1991 | Boschetti et al. | |
| 5,141,966 A | 8/1992 | Porath | |
| 5,185,313 A | 2/1993 | Porath | |
| 5,234,991 A | 8/1993 | Tayot et al. | |
| 5,268,097 A | 12/1993 | Girot et al. | |
| 5,563,056 A | 10/1996 | Swan et al. | |
| 5,652,348 A | 7/1997 | Burton et al. | |
| 5,700,630 A | 12/1997 | Inoue et al. | |
| 5,719,060 A | 2/1998 | Hutchens et al. | |
| 5,789,578 A | 8/1998 | Burton et al. | |
| 6,124,137 A | 9/2000 | Hutchens et al. | |
| 6,225,047 B1 | 5/2001 | Hutchens et al. | |
| 6,498,236 B1 | 12/2002 | Lihme et al. | |
| 6,572,767 B2 | 6/2003 | Stipanovic et al. | |
| 6,783,673 B2 | 8/2004 | Horsman et al. | |
| 7,144,743 B2 | 12/2006 | Boschetti et al. | |
| 2001/0045384 A1 | 11/2001 | Stipanovic et al. | |
| 2002/0014306 A1 | 2/2002 | Virtanen | |
| 2003/0008971 A1 | 1/2003 | Won et al. | |

FOREIGN PATENT DOCUMENTS

| | | |
|---|---|---|
| EP | 0 165 912 | 12/1985 |
| EP | 0 180 563 | 5/1986 |
| GB | 2 230 010 | 10/1990 |
| WO | WO 92/16292 | 10/1992 |
| WO | WO 95/31279 | 11/1995 |
| WO | WO 96/00735 | 1/1996 |
| WO | WO 98/08603 | 3/1998 |
| WO | WO 98/59360 | 12/1998 |
| WO | WO 03/064594 | 8/2003 |

OTHER PUBLICATIONS

International Search Report of PCT/US2004/008210.
G. H. Scholz et al., "Salt-Independent Binding Antibodies from Human Serum to Thiophilic Heterocyclic Ligands", *Journal of Chromatography B.*, 709:189-196, 1998.
S.C. Burton et al., "Hydrophobic Charge Induction Chromatography: Salt Independent Protein Adsorption and Facile elution with Aqueous Buffers", *Journal of Chromatography a*, 814:71-81, 1998.
L. Guerrier et al., "New Methods for the Selective Capture of Antibodies Under Physiological Conditions", *Bioseparation*, 9:211-221, 2000.
E. Boschetti et al., "The Use of Thiophilic Chromatography for Antibody Purification: A Review", *J. Biochem. Biophys. Methods*, 49:361-389, 2001.
Bo-Lennart Johansson et al., "Preparation and Characterization of Prototypes for Multi-Modal Separation Media Aimed for Capture of Negatively Charged Biomolecules at High-Salt Conditions", *Journal of Chromatography A*, 1016:21-33, 2003.
Bo-Lennart Johansson et al., "Preparation and Characterization of Prototypes for Multi-Modal Separation Aimed for Capture of Positively Charged Biomolecules at High-Salt Conditions", *Journal of Chromatography A*, 1016:35-49, 2003.

*Primary Examiner*—Long V. Le
*Assistant Examiner*—Shafiqul Haq
(74) *Attorney, Agent, or Firm*—Leydig, Voit & Mayer, Ltd.

(57) ABSTRACT

For certain mixed mode resins having anionic character, a ligand is joined to a solid support via a linkage that includes a mercapto-, ether- or amino-containing moiety. A suitable ligand comprises an aromatic group, a heteroaromatic group, or a heterocyclic group, optionally fused, that is sulfate-, sulfonate-, phosphonate- or phosphate-substituted and that is linked to such a moiety. These resins possess an anionic character under conditions prescribed for their use. Separation of a biological substance, such as a peptide or protein, can be accomplished with a resin of this type via a change in the pH of eluants, thereby effecting adsorption and desorption.

20 Claims, No Drawings

PREPARATION AND USE OF MIXED MODE SOLID SUBSTRATES FOR CHROMATOGRAPHY ADSORBENTS AND BIOCHIP ARRAYS

RELATED APPLICATIONS

This application is a divisional of U.S. Non-provisional Application No. 10/660,738 filed Sep. 12, 2003, now U.S. Pat. No. 7,144,743, which claims benefit from U.S. Provisional Application No. 60/410,273 filed Sep. 13, 2002.

BACKGROUND OF THE INVENTION

The present invention relates to solid substrates and to processes of making and using them in the context of separation science and analytical biochemistry.

The rapid development of and increasing need for proteins such as monoclonal and polyclonal antibodies have spawned a variety of techniques for isolating antibodies from solutions that contain them. Separation technologies such as precipitation methods, electrophoretic separations, and membrane filtration have been advanced to meet this need. The most promising technology is liquid chromatography.

Classic liquid chromatography techniques, utilizing adsorbents such as ion exchangers, hydrophobic supports, hydroxyapatite, and gel filtration media, are time-consuming and tedious to perform. Also, these techniques often lack the requisite specificity for separating heterogeneous mixtures of immunoglobulins.

Consequently, conventional techniques for separating proteins, such as immunoglobulins, have increasingly employed so-called affinity or pseudo-affinity chromatography techniques, which rely on specific interactions between an immobilized ligand and a particular molecule, such as a protein, to effect purification. Adsorbents comprising protein affinity ligands are generally effective, as described, for example, by Schwarz et at in WO 95/31279. Yet protein-based adsorbents can present serious drawbacks. Among these are: adverse interactions with biologically active eluants; the release of protein from a solid support, which results in contamination of the desired material; chemical and physical sensitivity (e.g., to extreme pH, detergents, chaotropics, high temperature) that discourages the requisite, frequent cleaning of columns, low selectivity; and prohibitively high cost.

Known pseudoaffinity-based separation methods employ a variety of lower molecular weight ligands to effect separation. See generally U.S. Pat. Nos. 5,652,348, 5,185,313, 5,141,966, 4,701,500 and 4,381,239. These techniques typically exploit one or both of hydrophobic and electrostatic interactions, to adsorb and desorb target molecules.

Hydrophobic-interaction chromatography generally requires the addition of lyotropic salts, which presents a significant disadvantage when large-scale separations are desired. Approaches that rely on electrostatic interactions between a target molecule and an adsorbent generally require pH adjustment of the feed stock.

Lowering the pH of feed stock will ionize some ligands, such that a target molecule will adsorb. In other scenarios at low pH, other target molecules will desorb. See E. Boschetti, *J. Biochem. Biophys. Methods* 49 (2001) 361. But acidic pH is not always desirable, since it may induce the formation of aggregates and reduce the biological activity of some molecules such as immunoglobulins. Despite the utility and low cost of some pseudoaffinity-based ligands, therefore, most methods that employ them suffer from low capacity and the need to change feed stock ionic strength, pH, or both.

In principle, powerful analytical methods can be realized with the affinity ligand adsorbents discussed above. For example, the rapid identification of disease markers by analyte/adsorbent interactions would As supplant the tedious and time consuming work required in conventional clinical diagnostics in order to prepare reagents that specifically bind to such markers. Additionally, the direct and rapid identification of differentially expressed proteins would be a significant benefit to the field, thereby circumventing, for example, the long process of polypeptide isolation and subsequent immunization to produce desired immunoglobulins. The above-mentioned shortcomings of conventional adsorbents limit the sensitivity and resolution of such analytical tools, however.

Accordingly, a need exists in the art for improved adsorbents that exhibit high binding capacity and specificity, that can be regenerated extensively without suffering physiochemical degradation, and that can function under physiological pH and/or ionic strength. A need also exists for improved biochemical analytic tools that are useful for the rapid identification of biologically important molecules.

SUMMARY OF THE INVENTION

To address these and other needs, the present invention provides a solid substrate that is comprised of a solid support; a monocyclic or polycyclic group that is heterocyclic, heteroaromatic, or aromatic and that is substituted with a sulfate, sulfonate, phosphate, or phosphonate group; and a linking group that comprises a mercapto-, ether-, or amino-containing moiety. The linking group links the monocyclic or polycyclic group to the solid support.

In accordance with one aspect of the invention, the solid substrate is an organic material. Preferably, the organic material is cellulose, agarose, dextran, polyacrylates, polystyrene, polyacrylamide, polymethacrylamide, copolymers of styrene and divinylbenzene, or mixtures thereof. Alternatively, the solid support is an inorganic material, preferably one selected from hydrogel-containing silica, zirconia, alumina, titania, ceramics, and mixtures thereof.

In one embodiment, the solid support is modified with a covalently coated silyl layer, which in turn covalently binds a cross-linked polysaccharide. The polysaccharide is preferably a copolymer of two polysaccharides, one of which is substituted with one or more cross-linking groups. Preferably, the polysaccharides in this regard include dextran, hydroxy-ethyl-cellulose, starch, amylase, and agarose, and most preferably are dextran. Suitable cross-linking agents include but are not limited to benzophenone groups.

The present invention can be implemented with a variety of linking groups, which comprise mercapto-, ether-, or amino-containing moieties. Moieties suitable for use in the linking group include alkylene groups, alkenylene groups, alkynylene groups, alkyl-oxy groups, aromatic groups, alkylaromatic groups, and combinations thereof. Preferably, the linking group is a mercapto alkyl group.

In accordance with another embodiment of the invention, the solid substrate comprises a polycyclic group. An acceptable polycyclic group is a heterocyclic or heteroaromatic group that is fused to an aromatic group. Preferred aromatic groups include phenyl, naphthyl, anthracenyl, phenanthrenyl, or acenaphthylenyl.

In some embodiments, the heterocyclic or heteroaromatic group described above comprises at least one sulfur (S) atom, or in the alternative, at least one nitrogen (N) atom.

The heterocyclic or heteroaromatic group may also comprise at least one S atom and one N atom. The invention further contemplates a heterocyclic or heteroaromatic group comprising at least two, three, or four N atoms. A preferred heterocycle that has four N atoms is represented by the formula:

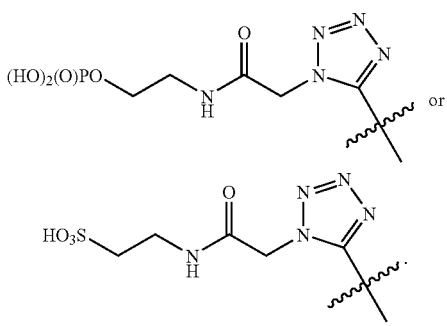

In certain embodiments, the heterocyclic or heteroaromatic group is a five- or six-member ring which is fused to an aromatic group. The fused rings are preferably represented by the formula:

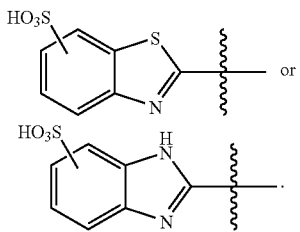

In these embodiments, the linking group is preferably an amino- or mercapto-containing moiety. A particularly preferred amino-containing moiety is represented by the formula:

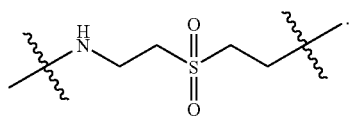

Particularly preferred mercapto-containing moieties are represented by the formulae:

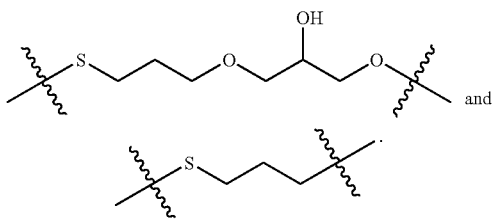

This invention further provides a method for separating biological substances from a sample. The method comprises contacting the solid substrate described above with a liquid sample that contains at least one biological substance, washing the resultant solid substrate with an equilibration buffer, then adjusting the pH so that the biological substance desorbs from the solid substrate. Preferably, the method is performed in the context of fixed bed, fluidized bed, or batch chromatography.

In one embodiment of the invention, the method further provides for the pH of the sample to be adjusted to a value where the biological substance adsorbs onto the substrate. Preferably, the pH is about 4 to about 6.

In yet another embodiment, the pH at which desorption of the biological substance occurs is adjusted to about 8 to about 11. A preferred embodiment provides for adjusting the pH of the sample to about 4 to about 6 and the pH at which the biological substance desorbs to about 8 to about 11.

The method is applicable to a variety of biological substances, which include proteins, viruses, nucleic acids, carbohydrates, and lipids. Preferably, the biological substance is a protein. More preferably, the protein is an immunoglobulin, hormone, clotting factor, cytokine, peptide, or enzyme. The most preferred protein is an immunoglobulin.

Yet another aspect of the invention concerns a process for making the solid substrate. The process comprises reacting the solid support with a bifunctional reagent, which comprises part or all of the linking group. The resultant product is then reacted with a reagent that comprises a heterocyclic, heteroaromatic, or aromatic group that is substituted with a sulfate, sulfonate, phosphate, or phosphonate group, thereby forming a bond between the heterocyclic, heteroaromatic, or aromatic group and the linking group. The bifunctional reagent comprises at least two functional groups, selected independently from each other, and which include but are not limited to bromide, iodide, an epoxide, carboxyl, an ester, aldehyde, a ketone, an amide, an alkene, cyano, and imino.

The present invention further provides a chromatography column, which comprises a tubular member having an inlet end and an outlet end. The column further comprises the present solid substrate, which is packed within the tubular member between first and second porous members disposed within the tubular member.

In one embodiment, the volume of the column is preferably between about 1 microliter or 1 milliliter and about 5000 liters. More preferably, the column volume is between about 1 liter and 100 liters. In another embodiment, the column further comprises one or more fluid control devices for flowing a liquid sample upward through the solid substrate. In yet another embodiment, the column further comprises a series of stages between the inlet and outlet ends.

According to another aspect of the invention, the solid substrate is in the form of a biochip. In this context, the solid support can be a metal, silicon, glass, or an organic polymer. In one embodiment, the solid substrate is a mass spectrometer probe. In another embodiment, the monocyclic or polycyclic group is linked to the biochip at a plurality of addressable locations. In yet another embodiment, the linking group of the solid substrate further comprises a polysaccharide.

Alternatively, the solid support is a chip. The support may further comprise a covalently attached layer to which is covalently bound a cross-linked polysaccharide layer. In some embodiments, the cross-linked polysaccharide is a copolymer of a first polysaccharide and a second polysaccharide that is substituted with one or more cross-linking groups. A preferred cross-linking group is a benzophenone group. The polysaccharides are preferably chosen from dextran, hydroxy-ethyl-cellulose, starch, amylase, and agarose. Dextran is the most preferred polysaccharide.

In other embodiments, the linking groups link a monocyclic or polycyclic group to the solid substrate at a plurality of addressable locations on the chip. In some instances, two or more different addressable locations comprise the same linking and monocyclic or polycyclic groups. A preferred solid support in this context is alumina or silica.

This invention also provides a method of detecting an analyte by contacting an addressable location of the solid substrate described above with a sample that comprises the analyte, whereby the analyte is affixed to the solid substrate. The solid substrate is then introduced into a probe interface of a laser desorption mass spectrometer in such a way as to position the addressable location proximately to a laser beam in the mass spectrometer. The solid substrate is irradiated at the addressable location with a laser pulse for a time and power sufficient to desorb and ionize the analyte, which is then detected with the mass spectrometer. The analyte is a biological substance as described above.

DETAILED DESCRIPTION OF THE PREFERRED EMBODIMENTS

The present invention provides a solid substrate that is an effective adsorbent for use in separating and isolating a variety of biological substances. The solid substrate of this invention may be used, for example, in preparative techniques, such as column chromatography, and in analytical devices, such as biochips. One advantage of the present solid substrate described herein is its high selectivity and specificity for biological substances such as immunoglobulins, together with the avoidance of costly and often detrimental cleaning processes required for prior art substrates. A second advantage is that the solid substrate of this invention is ideally suited for use with biological samples at physiological pH and ionic strength, thereby obviating the need for pH adjustment and the addition of lyotropic salts as prescribed in the prior art. A third advantage is the high capacity of the present substrates, which, in view the low cost of reagents employed to prepare them, presents significant economic gains over the use of specialized prior art adsorbents.

Mixed Mode Ligand

The solid substrates of this invention comprise a solid support and a ligand attached to the solid support. The ligand comprises a cyclic group which can be a monocyclic group or a polycyclic group, and a linking group that optionally comprises a sulfur atom. The ligand that attracts analytes through a mixed mode action, attached to a solid support.

The ligand comprises a cyclic group, which can be a monocyclic or polycyclic group that is tethered to the solid support and that is substituted by a sulfate, sulfonate, phosphate, or phosphonate group. This monocyclic or polycyclic group can be an aromatic group, which, as defined here, is a cyclic hydrocarbon containing only unsaturated carbon-carbon bonds to give an aromatic system. While any aromatic group, in principle, may be employed in the present invention, a suitable aromatic group typically comprises one, two, or three aromatic rings. Thus, illustrative aromatic groups are phenyl and its substituted derivatives, such as tolyl and xylyl. Bicyclic aromatic groups comprise fused individual rings, and include but are not limited to naphthyl. Polycyclic aromatic groups include anthracenyl and phenanthrenyl, and groups such as acenanaphthylenyl that contain fused rings of different sizes. If an aromatic group is selected, it is preferred although not essential that the group be fused to a heterocyclic or heteroaromatic group, as described below.

A "heterocycle" is a saturated to partially saturated ring containing at least one hetero atom. Similarly, a "heteroaromatic group" is an aromatic group in which at least one carbon atom is substituted by a heteroatom. In the present invention, the hetero atom preferably is N, S, or O. It also is preferable that the heterocyclic or heteroaromatic group is a five- or six-member ring, as reagents that comprise these groups are readily and inexpensively obtained from commercial sources.

When a linking group, as defined below, does not contain a bivalent sulfur atom, then it is preferred that the heterocyclic or heteroaromatic group is one that establishes or contributes to the "thiophilic" character of the solid substrate, and is thus one that contains at least one S atom. With the use of other linker groups that contain bivalent sulfur atoms, preferable heterocyclic or heteroaromatic groups may comprise at least one N atom, or combinations of S and N atoms.

Thus, exemplary heterocyclic or heteroaromatic groups include thiazoline, thiazolidone, imidazole, imidazoline, thiazole, triazoles, tetrazole, thiadiazole, imidazole, pyridine, and morpholine. In a particularly preferred embodiment, a suitable heterocyclic or heteroaromatic group is fused to an aromatic group, as described above. In this context, benzimidazole and benzothiazole are the readily available candidates, yielding superior solid substrates.

As mentioned above, the monocyclic or polycyclic group is substituted with a sulfate, sulfonate, phosphate, or phosphonate group. These groups are sufficiently acidic to exist as charged moieties within a large pH range, e.g., from about 2 to about 12. In this context, the solid support is ideally suited to adsorb biological substances such as immunoglobulins at physiological ionic strength and pH.

The term "substituted," as used herein, refers to the direct or indirect attachment of a sulfate, sulfonate, phosphate, or phosphonate group to the monocyclic or polycyclic group. Indirect attachment can occur through a spacer group, which is a $C_{1-6}$ straight or branched alkylene group. The alkylene group is optionally interrupted by one or more bivalent moieties that include but are not limited to —C(O)NH—, —NHC(O)—, —O—, —S—, —S(O)—, —S(O)$_2$—, —NH—, —C(O)O—, and —OC(O)—. Thus, illustrative spacer groups include —CH$_2$—, —CH$_2$CH$_2$—, —CH$_2$—O—CH$_2$—, and —CH$_2$C(O)NHCH$_2$CH$_2$—.

The monocyclic or polycyclic group is tethered to the solid support by a linking group, which comprises a mercapto-, ether-, or amino-containing moiety. Subject to structural considerations described below, it is preferred that the linking group is hydrophobic, thereby conferring hydrophobic character to the solid support at a pH where binding of a biological substance occurs through both electrostatic and hydrophobic interactions. Hydrophobic moieties include but are not limited to straight and branched $C_{1-6}$ alkylene groups, $C_{2-6}$ alkenylene groups, and $C_{2-6}$ alkynylene groups. Particularly useful moeities are ethylene and propylene. Other hydrophobic moieties comprise an aromatic group, as described above, to form, for example, phenethylene. The foregoing moieties are thus interrupted or capped by at least one mercapto, ether, or amino moiety. In embodiments where the monocyclic or polycyclic group does not comprise a sulfur atom, the linking group preferably contains a mercapto moiety. In this respect, the linking group confers hydrophobic and thiophilic characters to the solid substrate. One preferred mercapto-containing linking group is represented by the formula:

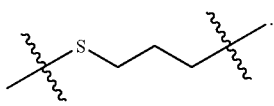

The hydrophobicity of the linking group can be readily tailored by introducing polar substituents, such as hydroxyl, a halide, or nitro; by oxidizing a mercapto moiety by known methods; by incorporating ether or amino moieties into the linking group; or combinations thereof. Thus, one such mercapto-containing linking group that is readily accessed is represented by the formula:

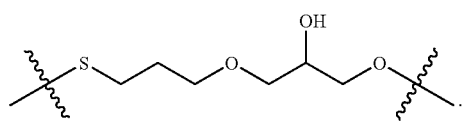

An illustrative amino-containing linking group is represented by the formula:

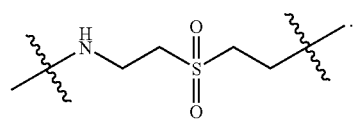

Preferably, the solid substrates comprised of amino-containing linking groups, or those containing oxidized mercapto moieties, also comprise monocyclic or polycyclic groups that comprise at least one S atom. In this respect, the solid substrate is able to retain some thiophilic character. In another preferred embodiment, the linking group itself comprises a polysaccharide such as hydroxy-ethyl-cellulose, starch, amylose, or agarose. A preferred polysaccharide in this context is dextran. Thus, the solid support is modified with a polysaccharide, which can be derivatized with a linking group as described below.

Without limiting themselves to any particular theory, the inventors believe that the solid substrate of this invention operates via "mixed modes" of interaction between the solid substrate and a biological substance. The aforementioned monocyclic and polycyclic groups have a pK below 4 and, hence, are negatively charged within the pH ranges of use as described above. A biological substance, such as an immunoglobulin, is contacted with the solid substrate between about pH 4 and pH 6, in which range the biological substance bears a net positive or neutral charge. In this pH range, the biological substance binds to the solid substrate through one or more types of interactions with the mono- or polycyclic groups. The interactions include coulombic attractions and mild hydrophobic associations. When the pH is raised above about 8, the biological substance gains a net negative charge, thereby creating electrostatic repulsion between the negatively charged solid substrate and the negatively charged biological substance. Consequently, the biological substance is released by the electrostatic repulsion from the solid substrate and can then be isolated. It is believed that these repulsive ionic forces are greater than the weaker attractive forces noted above.

Solid Substrate

This invention contemplates a solid support to which the mixed mode ligand is attached. Two different formats are contemplated in particular. In one format, the solid support is of the form typically used for chromatography media, that is, a bead or particle. These beads or particles are derivatized with the mixed mode ligand. The beads or particles form a chromatography medium that one can use to pack the column. In another format, the solid support takes the form of a chip, that is, a solid support having a generally planar surface to which the mixed mode ligand can be attached, covalently or otherwise. Chips that are adapted to engage a probe interface of a detection device such as a mass spectrometer are also called "probes."

Beads And Particles

In accordance with the teachings of this invention, the solid substrate first comprises a solid support, which may comprise an organic material. Exemplary organic materials are polysaccharides, such as cellulose, starch, agar, agarose, and dextran. Hydrophilic synthetic polymers are contemplated, including substituted or unsubstituted polyacrylamides, polymethacrylamides, polyacrylates, polymethacrylates, polyvinyl hydrophilic polymers, polystyrene, polysulfone, and copolymers or styrene and divinylbenzene. Alternatively, inorganic materials may be used as the solid support material. Such inorganic materials include but are not limited to porous mineral materials, such as silica; hydrogel-containing silica, zirconia, titania, alumina; and other ceramic materials. It is also possible to use mixtures of these materials, or composite materials formed by copolymerization of or by an interpenetrated network of two materials, such as those disclosed in U.S. Pat. Nos. 5,268,097, 5,234,991, and 5,075,371.

The solid support may be in the form of beads or irregular particles of about 0.1 mm to about 1000 mm in diameter. Alternatively, the solid support can be fashioned into fibers, membranes, or sponge-like materials permeated with holes in the micron to multi-millimeter sizes.

The monocyclic or polycyclic groups described above are chemically immobilized on the solid support by forming covalent bonds between the solid support and the linking group, and between the linking group and monocyclic or polycyclic groups. In-typical scenarios, the solid support is first treated with a bifunctional reagent which serves to introduce onto the solid support reactive groups that form part or all of the linking group. For some solid supports, such as cellulose, composites containing a hydrogel, or other materials presenting hydroxyl groups, it is often advantageous to deprotonate the hydroxyl groups with a hydroxide source, for example, prior to reaction with a bifunctional reagent. The bifunctional reagent is capable of reacting both with the solid support and with reagents that contain the monocyclic or polycyclic groups. Illustrative bifunctional reagents, which contain the same or different functional groups, include but are not limited to epichlorhydrin, epibromhydrin, dibromo- and dichloropropanol, dibromobutane, ethylene glycol diglycidylether, butanediol diglycidylether, divinyl sulfone, allylglycidylether, and allyl bromide.

Once functionalized, the solid support is then washed extensively with one or more solvents to remove unreacted bifunctional reagent, reaction byproducts, or both. A typical solvent used in this regard is water.

The monocyclic or polycyclic groups then are introduced by way of reagents that contain such groups substituted with mercapto, hydroxyl, or amino groups. Such reagents react with functional groups presented by the functionalized solid support as described above.

The particular pairing of a bifunctional reagent with a monocyclic or polycyclic reagent is guided by well-known chemistries. For example, solid supports that are functionalized with epoxides may undergo reactions with mercapto, hydroxy, or amino-containing reagents to furnish a substrate with ethylene-containing linking groups. Other solid supports modified with allyl bromide, for example, present alkene groups that can be reacted directly with mercapto-containing reagents. Alternatively, the alkene groups can be further brominated to furnish suitably reactive bromo derivatives.

The concentration of immobilized monocyclic or polycyclic group can vary between a fraction of a micromole to several hundred micromoles per milliliter of solid support, depending upon the concentration of bifunctional reagent used to make the solid support. Low concentrations of the immobilized group typically result in low separation capacity of the solid substrate, whereas high concentrations generally lead to increased capacity.

Biochip

A preferred embodiment has the solid substrate, thus described, in a "biochip" or microarray format, where the substrate presents a generally planar surface to which is attached a capture reagent: in the present context, a combination of a linking group and a monocyclic or polycyclic group. Thus, a biochip presents a defined region or site—more typically, a collection of defined regions or sites—on which analytes may be captured selectively. Upon capture, analytes can be detected and, optionally, characterized by a variety of techniques, described in more detail below.

Thus, the solid support can comprise a metal, such as gold, aluminum, iron, titanium, chromium, platinum, copper and their respective alloys. Such metals can be derivatized on their surfaces with silicon dioxide, for instance, to provide reactive groups for linking. One method of derivatizing a metal surface is to sputter a metal oxide, such as silicon oxide, onto the metal surface. Alternatively, the solid support can comprise silicon, glass or an organic polymer, such as a plastic. In certain embodiments, the solid support can be transparent.

The basic solid substrate of this invention comprises a solid support, to which a capture layer is linked, either directly or indirectly. The capture layer comprise individual linking groups that tether chemical moieties to the solid support. The chemical properties of the linking groups and chemical moieties combine to selectively attract biological substances under certain conditions, as described fully below. The substrate may comprise, in addition to the solid support, an intermediate layer through which the capture layer is linked indirectly to the solid support.

According to certain embodiments of this invention, the solid support is modified with sequential silyl and cross-linked polysaccharide coatings. The silyl coating is covalently attached to the surface of the solid support. This coating results from depositing onto the solid support one or more silanes (usually polyalkyloxy silanes such as methoxy or ethoxy) that can react with the surface of the solid support as disclosed, for example, in copending U.S. application Ser. No. 10/412,769. Suitable silanes in this regard include but are not limited to (3-acryloxypropyl)trimethoxysilane, (3-acryloxypropyl)methyidimethoxysilane, (3-acryloxypropyl)dimethylmethoxysilane, (3-acryloxypropyl)trichlorosilane, (3-acryloxypropyl)methyldichlorosilane, (3-acryloxypropyl)dimethylchlorosilane, (3-methacryloxypropyl)trimethoxysilane, (3-methacryloxypropyl)methyidimethoxysilane, (3-methacryloxypropyl)dimethylmethoxysilane, (3-methacryloxypropyl)trichlorosilane, (3-methacryloxypropyl)methyldichlorosilane, (3-methacryloxypropyl)dimethylchlorosilane, vinyltrichlorosilane, vinyltrimethoxysilane, allylchloromethyldimethylsilane, allylchlorodimethylsilane, allylbromodimethylsilane, allyldichloromethylsilane, allyldiisopropylaminodimethylsilane, allyloxy-tert-butyldimethylsilane, allyltrimethoxysilane and combinations thereof.

The silylated solid support of this embodiment thus enables the subsequent covalent attachment of a layer comprising a cross-linked polysaccharide. The cross-linked polysaccharide may be viewed as a copolymer of a first polysaccharide and a second polysaccharide that is substituted with cross-linking groups. Thus, the cross-linking groups give rise, upon activation, not only to the cross-linking of polysaccharides themselves, but-also to covalent attachment of the polysaccharides to the silylated solid support.

Suitable second polysaccharides in this regard are those that are substituted by N,N'-methylene-bis-acrylamide, N,N'-methylene-bis-methacrylamide, diallyltartardiamide, or benzophenones such as 4-carboxyl-benzophenone. The crosslinking agent may be a bis-epoxide cross-linker, such as butane diol diglycidyl ether (BDDGE), ethylene glycol diglycidyl ether (EDGE), or poly(ethylene glycol)diglycidyl ether (PEGDGE). Activation may therefore occur by chemical means (e.g., polymerization) or photochemical means, such as irradiation by UV or near-UV light. The latter activation means is especially useful for polysaccharide coatings that are substituted with photosensitive cross-linking groups such as benzophenones.

Notably, the arrangement of sites on the surface of a biochip of the invention preferably permits interrogation of multiple sites at the same time, to achieve higher throughput and speed. The use of a biochip is therefore essentially equivalent to concurrently conducting multiple chromatographic experiments, each with a different chromatographic column, but the present biochip has the advantage of requiring only a single system.

Thus, it is preferable that an inventive biochip comprise a plurality of addressable locations, and to each such location is tethered a unique combination of linking group and monocyclic or polycyclic group. The biochip can incorporate a single addressable location or as many as 10, 100, 1000, 10,000 or more addressable locations, which need only be as large as an impinging energy source, such as a laser. In this regard, "addressable" connotes a position on the solid substrate that can be located, e.g., by an energy source, using an appropriate addressing scheme or algorithm. Thus, each addressable location or subsets of locations can bind a biological, substance preferentially, and the binding can be located by virtue of the fact that capture occurs at a defined location on the biochip.

The addressable locations can be arranged in any pattern but preferably appear in regular patterns, such as lines or orthogonal arrays, or even as curves, such as circles. Circular arrangements of the addressable locations are particularly useful on disk-shaped biochips. Thus arranged, the addressable locations can provide known gradients of binding capacity on the solid substrate. In a particularly preferred embodiment, the present solid substrate in the form of a biochip is a probe for use in a detection instrument, such as a mass spectrometer, therewith providing a powerful analytic tool for the capture and identification of known and unknown biological analytes. Illustrative probes are described in U.S. Pat. No. 6,225,047, which is incorporated herein by reference. For example, a mass spectrometer probe ("MS probe") refers to a device that, when positionally engaged in an interrogatable relationship to an ionization source, e.g., a laser desorption/ionization source, and in concurrent communication at atmospheric or subatmospheric pressure with the detector of the preferred Laser Desorption/Ionization Time-Of-Flight spectrometer, can be used to introduce ions derived from an analyte into the spectrometer. Preferred laser sources include nitrogen lasers, Nd-Yag lasers and other pulsed laser sources. Thus, a MS probe typically is reversibly engageable (e.g., removably insertable) with a probe interface that positions the MS probe in an interrogatable relationship with the ionization source and in communication with the detector.

For some embodiments, the solid support of the biochip is first modified with silyl and cross-linked polysaccharide layers. In these cases, it is preferable to react one or more silanes as described above with the solid support, for example, by using chemical vapor deposition to deposit a layer of the silane. Attachment of the cross-linked polysaccharide layer can proceed by either of two primary ways. In a typical scenario, the first polysaccharide is derivatized at a plurality of hydroxyl groups with linking groups and monocyclic or polycyclic groups as described above in the general method for making the solid substrate with an unmodified solid support. Continuing, the second polysaccharide is substituted with cross-linking groups using conventional organic chemistry. A preferred cross-linking group is 4-carboxyl-benzophenone. The first and second polysaccharides are then contacted with the silylated solid support and subjected to chemical or photochemical conditions that initiate cross-linking between the polysaccharides and the silylated solid support.

In an alternative approach, a polysaccharide that is substituted with cross-linking groups, optionally together with an unsubstituted polysaccharide, is similarly cross-linked and attached to the silylated solid support. The resultant cross-linked polysaccharide layer presents hydroxyl groups that are derivatized with linking groups and monocyclic or polycyclic groups.

In another embodiment the chip comprising an attached mixed mode ligand is adapted for SEND (Surface Enhanced Neat Desorption). This is accomplished by attaching to the surface molecules that absorb laser energy and promote desorption and ionization of an anayte into the gas phase. The energy absorbing molecules are attached to the surface in such a manner that they do not envelop the analyte in a matrix crystal and they are not desorbed upon contact with ionizing energy. SEND is further described in U.S. Pat. No. 6,124,137 (Hutchens and Yip) and WO 03/064594 (Kitagawa).

Method of Separating Biological Substances

The solid substrates of the present invention can be used to separate and isolate a variety of biological substances, such as proteins, viruses, nucleic acids, carbohydrates, and lipids. The biological substances typically derive from, or are contained in, sources including but not limited to liquid samples such as saliva, blood, urine, lymphatic fluid, prostatic fluid, seminal fluid, milk, milk whey, organ extracts, plant extracts, cell extract, cell culture media, fermentation broths, serum, ascites fluid, and transgenic plant and animal extracts.

In this context, a particularly preferred class of biological substances is immunoglobulins. The "immunoglobulins" category embraces whole immunoglobulins, including monoclonal and polygonal antibodies, as well as Fab, $F(ab')_2$, $F_c$ and $F_v$ fragments thereof.

The liquid sample containing one or more biological substances is contacted with the solid substrate of this invention for a period of time sufficient to allow at least one biological substance to bind to the solid substrate. Typically, the contact period is between about 30 seconds to about 12 hours.

An advantage of the present invention is that the pH, ionic strength, or both of the liquid sample need not be adjusted prior to contacting the sample with the solid substrate. Additionally, it is not necessary to concentrate, dilute, or mix the sample with additives such as salts. Many liquid samples, such as milk whey, are already slightly acidic (e.g., pH 5-5.5) where the sulfate, sulfonate, phosphonate, or phosphate groups of the solid substrate are charged, and are thus poised to enhance the adsorption of certain proteins. Thus, direct loading of a liquid sample onto the solid substrate of this invention is possible. The pH of other liquid samples can be adjusted, however, to within about pH 4 to about 6 if necessary.

The temperature at which the liquid sample is contacted with the solid substrate varies between samples and a given solid substrate. Preferably, the temperature is ambient, but can be changed.

After the sample is contacted with the solid substrate, the solid substrate is washed with an equilibration buffer. As defined herein, an equilibration buffer is a buffer that is preferably of the pH at which the liquid sample was contacted with the solid support. Furthermore, the equilibration buffer washes from the solid support any substance that does not adsorb to the substrate. Suitable equilibration buffers include acetate buffer and phosphate buffered saline. The washing may be accomplished by bathing, soaking, or dipping the solid substrate with bound biological substance into the equilibration buffer. Alternatively, the equilibration buffer may be rinsed, sprayed, or washed over the solid substrate.

The desired biological substance typically is one that adsorbs to the solid substrate. However, the invention contemplates scenarios in which the biological substance of interest is removed in the equilibration buffer washing. In this case, the substance may be isolated by routine methods from the buffer.

Biological substances which are adsorbed to the solid substrate are then desorbed by adjusting the pH to a value where the substance can desorb. Although the pH at which desorption occurs will vary from substance to substance, the pH is preferably in the range of about 8 to about 11. In this context, the desorption process is particularly amenable to proteins which degrade at low pH values, where prior art methods are performed. The pH can be adjusted by any routinely available reagent, such as aqueous solutions of Tris-HCl or carbonate buffers. The desorbed biological substance is then collected. Typical purities of biological substances, such as antibodies, that are purified by the method of this invention range from about 70% to about 99%, preferably 85% to about 99%, and most preferably about 90% to about 99%.

The separation method described above can be adapted for use in a variety of techniques, including preparative methods employing fixed bed, fluidized bed, and batch chromatographies. Alternatively, the method can be practiced in the context of high throughput separation techniques that utilize small devices such as spin columns or multiwell plate formats where device volumes can be as small as a few microliters.

The techniques mentioned above comprise contacting a solution containing the biological substances with the solid substrate, thereby leading to the selective adsorption of at least one biologicial substance in the solution by the solid substrate. In the event of the desired biological substances) being fixed to the resin, the elution of the latter allows it or them to be separated and collected in a purified and concentrated form. If the desired biological substance remains in the treated solution (the other biological substances being fixed to the solid substrate) then the desired separation is obtained directly by collecting the eluant.

When using batch adsorption/separation, the solid substrate is added directly to the solution of biological substances, and the solid substrate/biological subtance mixture is gently agitated for a time sufficient to allow the biological substances to bind to the solid substrate. The solid substrate, with adsorbed biological substances, may then be removed by centrifugation or filtration, and the biological substances subsequently eluted from the solid substrate in a separate step.

Alternatively, column chromatography may be used. In fixed bed column chromatography, the solid substrate is packed into a column, and the solution which contains the biological substances to be separated is applied to the solid substrate by pouring it through the sorbent at a rate that allows the biological substances to bind to the solid substrate.

Advantages of fixed bed chromatography include minimal column volume and water consumption. The disadvantage of the column chromatography method is that the flow rate of liquids through the column is slow, and, therefore, time-consuming. This flow rate can be reduced even further if the material being applied to the column includes particulates, since such particulate material can "clog" the solid substrate to some degree.

In fluidized bed column chromatography, a rising filtration flow and large/dense particles are used in order to maintain an equilibrium against the rising forces. An essentially vertical column composed of between 1 and 5 stages placed on top of the other is used, and the solution successively passes through stage and is drawn off by an overflow on the upper part of the upper stage. Preferably, the column has three stages. Each stage, with the exception of the uppermost one, is separated by two distribution systems, one distributing the solution at the base of the stage in question, the other distributing the solution towards the stage located immediately above.

The advantages of a fluidized bed are higher flow rates at lower pressures as compared to fixed bed chromatography. Although the higher flow rates offer certain advantages to the chromatographic separation, the method has several shortcomings. The method requires either large particle diameter and/or high density resins that expand only under high upward liquid velocity. Large diameter resins have less surface area per unit volume than small resins used, and correspondingly have less surface binding capacity. This is why small bead resins are preferred, in which case the bead resins must be highly dense.

On the other hand, fluidized bed chromatography avoids many of the serious disadvantages of fixed beds, which include clogging, need for cleaning, compression and cleaning-induced resin deterioration. In fact, the fluidized bed allows free passage of solid impurities in the solution with no risk of clogging; less stringent cleaning is necessary so the life-span of the resins is greatly increased. However, the chromatographic sorbents for biological substances typically are not suitable for fluidized bed chromatography, having a density too close to that of water or being too small in granulometry. This makes it impossible to fluidize without drawing particles into the flux. Another problem with fluidized bed chromatography of biological substances relates to the large space between beads, which would result in a decrease in efficiency.

In view of these factors, batch and fixed bed chromatography have been the methods of choice in prior art separation techniques for biological substances. The present solid substrate, on the other hand, can be used in batch, fixed bed, or fluidized bed chromatography.

Thus, in a preferred embodiment, the present invention provides a chromatography column, which is a tubular member packed with the solid substrate described herein. The tubular member can be made of any suitable material, such as glass, plastic, or metal. The packed solid substrate is abutted on each end by porous members that keep the substrate fixed within the tubular member.

In some embodiments, gravity flow of an eluant through a column is sufficient. In other embodiments, the column may comprise one or more fluid moving devices to achieve an upward flow of eluant through the column. Such devices include pumps, injectors, and any other device typically employed in association with chromatography equipment.

The chromatography column of this invention can be of any volume. For example, separations on a laboratory scale may warrant a column volume as small as about 1 milliliter or even about 1 microliter. Large scale purification and isolation of biological substances can be performed on columns as large as 5000 liters. More typical volumes are between 1 liter and 100 liters. The column is tubular in general shape, but is not otherwise particularly limited in length or diameter. Depending upon the context in which the column is employed, the column diameter can vary between about 0.5 mm to about 1000 mm. Additionally, the column length can vary between about 50 mm to about 1000 mm. Thus, the invention contemplates columns of a variety of dimensions and corresponding volumes.

The column of this invention can be used in tandem with columns comprising other solid substrates, which would be effective in eliminating different impurities from a sample. Thus, the advantages of the present column can be viewed as being complementary to the characteristics of other or conventional columns. In this context, such a tandem arrangement of columns would conserve eluants and equilibration buffer, thereby eliminating the need for additional sample manipulation and preparation.

Method of Detecting an Analyte

This invention thus provides a convenient method of detecting an analyte. An addressable location of the biochip as described above is contacted with a sample that contains at least one analyte. The analyte is a biological substance, such as those described herein, which adsorbs to (i.e., is captured at) the addressable location. The present method thus accommodates the detection of a plurality of analytes contained in a single sample, each analyte being bound to a unique location on the biochip.

The biochip is then preferably washed with an eluant as described above to remove unbound materials. In this context, the introduction of eluant to small diameter spots of the solid substrate is best accomplished by a microfluidics process.

Detection of analytes that remain bound to the biochip can be accomplished by a variety of methods. These include microscopy and other optical techniques, mass spectrometry, and electrical techniques. Light-based detection parameters include, for example, absorbance, reflectance, transmittance, birefringence, refractive index, and diffraction measurement techniques.

Fluorescence detection of labeled analytes is particularly popular. Methods involving fluorescence include direct and indirect fluorescent measurement. Specific methods include, for example, fluorescent tagging in immunological methods such as ELISA or sandwich assay.

Other useful techniques include, for example, surface plasmon resonance, ellipsometry, resonant mirror techniques, grating coupled waveguide techniques, multipolar resonance spectroscopy, impedimetric detection, chemiluminescence detection, and electrical conductivity/reduction—oxidation methods. Methods of desorbing and/or ionizing analytes from biochips for direct analysis are well known in the art, and are generally described, for example, in U.S. Pat. No. 6,225,047.

A particularly preferred method of analysis is Surface-Enhanced Laser Desorption/Ionization ("SELDI"), which is described in, for example, U.S. Pat. Nos. 5,719,060 and 6,255,047. In SELDI, an addressable location on the biochip is presented to an energy source such as a laser, which desorbs and ionizes the analyte bound at the addressable location. The ionized analyte is then detected directly in a time-of-flight ("TOF") mass spectrometer, for example, thereby yielding the mass-to-charge ratio of the desorbed analyte. By repeatedly shifting and positioning the biochip within the probe interface to align with the laser, each addressable location on the biochip can be similarly analyzed.

Additionally, an ion mobility spectrometer can be used to analyze samples. The principle of ion mobility spectrometry is based on different mobility of ions. Specifically, ions of a sample produced by ionization move at different rates, due to their difference in, e.g., mass, charge, or shape, through a tube under the influence of an electric field. The ions, which are typically in the form of a current, are registered at the detector which can then be used to identify the sample. One advantage of ion mobility spectrometry is that it can operate at atmospheric pressure.

Furthermore, a total ion current measuring device can be used to analyze samples. This device can be used when the probe has a surface chemistry that allows only a single class of analytes to be bound. When a single class of analytes is bound on the probe, the total current generated from the ionized analyte reflects the nature of the analyte. The total ion current from the analyte can then be compared to stored total ion current of known compounds. Therefore, the identity of the analyte bound on the probe can be determined.

An advantage of the biochips and analytical method of this invention is that binding and detecting analytes are effective in picomolar or even attomolar amounts of analyte. In accordance with the teachings of this invention, it is thus possible to discover certain subclasses of biological substances referred to as biomarkers. In the present context, a biomarker is an organic biological substance, particularly a polypeptide or protein, which is differentially present in a sample taken from a diseased subject as compared to a sample taken from a healthy subject. A biomarker is differentially present in samples taken from diseased subjects if it is present at an elevated level or a decreased level relative to the level present in a sample taken from a healthy subject.

The solid substrate of the present invention, particularly in the form of a biochip, allows the rapid discovery and identification of biomarkers.

This method is useful for protein profiling, in which proteins in a sample are captured using one or more different solid substrates of this invention and then the captured analytes are detected. In turn, protein profiling is useful for difference mapping, in which the protein profiles of different samples are compared to detect differences in protein expression between the samples.

The following examples are given to illustrate the present invention. It should be understood, however, that the invention is not to be limited to the specific conditions or details described in these examples. All references to publicly available documents, including patents, are incorporated herein by reference as if set forth fully in their entireties.

EXAMPLE 1

Immobilization of Mercapto-Benzimidazole Sulfonic Acid ("MBISA") on Cellulose Beads The purpose of this example is to demonstrate the preparation of a solid substrate comprised of a mercapto-alkyl linking group.

Wet cellulose beads (100 g) were washed extensively with water to eliminate salts and preservatives. The beads were treated sequentially with 100 ml of a 1 M sodium hydroxide solution, and with vigorous shaking, 10 g of allyl-bromide. The mixture was stirred overnight at room temperature to ensure complete reaction. The derivatized beads were then washed extensively with water to remove excess reagents and by-products.

The allyl-cellulose derivative was treated with 100 ml of deionized water, 5 g of N-bromosuccinimide, and 8.3 g of potassium bromide. The resultant suspension was agitated and then treated with phosphoric acid to adjust the pH to 3.8-4.0. The mixture was further agitated for 1 hour at room temperature and then washed with water.

To the resultant brominated derivative of the cellulose beads were added 2.7 g of MBISA dissolved in 80 ml of water at pH 10 (by addition of sodium hydroxide). The suspension was stirred for 16 hours at room temperature and then washed extensively with water until excess reagents and by-products were eliminated to yield the desired solid substrate.

EXAMPLE 2

Immobilization of MBISA on Cellulose Beads via a Mixed Mercapto- and Ether-Containing Linker The purpose of this example is to demonstrate the preparation of a solid substrate comprised of a mercapto-and ether-containing linking group.

Cellulose beads (100 g) were washed as in Example 1. The beads were treated sequentially with 40 mL of a solution 0.5 M sodium hydroxide, 25 ml of ethanol, and 20 g of allylglycidyl-ether with shaking. The mixture was stirred overnight at room temperature to ensure complete reaction. The derivatized beads were then washed extensively with water to remove excess reagents and by-products.

The desired product was obtained by bromination and then treatment with MBISA according to the procedure in Example 1.

EXAMPLE 3

Immobilization of Mercapto-Benzimidazole Sulfonic Acid (MBISA) on Zirconium Oxide Composite Beads This example demonstrates the preparation of a solid substrate comprised of a composite solid support material.

A composite resin (100 g) of wet porous zirconium oxide beads containing within the pores a hydrogel of 5% agarose was washed extensively with water. The beads then were treated with 50 ml of 1 M sodium hydroxide and, with vigorous shaking, 5 g of allyl-bromide. The mixture was stirred overnight at room temperature to ensure complete reaction. The derivatized beads were then washed extensively with water to remove excess reagents and by-products.

The allyl-cellulose derivative was then treated with a solution of 2 g of N-bromosuccinimide and 4 g of potassium bromide in 50 ml of demineralised water. Under agitation, the suspension was further treated with 0.5 gram of 85% phosphoric acid. The mixture was agitated for 1 hour at room temperature and then washed with water.

The resultant brominated derivative was treated with a solution of 4 g of MBISA in 80 ml of water solution at pH 10 (by addition of sodium hydroxide).

The suspension of the desired solid substrate was stirred for 5 hours at room temperature, then washed extensively with 1 M sodium hydroxide and water until excess reagents and by-products were eliminated.

EXAMPLE 4

Immobilization of Amino-Benzimidazole Sulfonic Acid (ABISA) on Cellulose Beads The purpose of this example is to demonstrate the preparation of a solid substrate comprised of an amino-containing linking group.

Wet cellulose beads (100 g) were washed extensively with water to eliminate salts and preservatives. The beads were treated sequentially with 100 ml of a 0.5 M sodium hydroxide solution, and with vigorous shaking, 10 gram of divinylsulfone. The mixture was stirred overnight at room temperature to ensure complete reaction. The derivatized beads were then washed extensively with water to remove excess reagents and by-products.

The vinylsulfone-cellulose derivative was then treated with 100 ml of 0.1 M sodium hydroxide solution containing 3 gram of ABISA (pH was maintained at least at 10 by addition of sodium hydroxide). The suspension was agitated for 16 hours at room temperature and then washed extensively with water to eliminate excess reagents and by-products, thereby furnishing the desired solid substrate.

EXAMPLE 5

Immobilization of Amino-Benzothiazole Sulfonic Acid (ABTSA) on Cellulose Beads The purpose of this example is to demonstrate the preparation of a solid substrate comprised of an amino-containing linking group and sulfur-containing polycyclic heterocycle.

The procedure as described in Example 4 can be followed to prepare vinylsulfone-cellulose beads, which can then be treated with 3 gram of ABTSA in 100 mL 0.1 M sodium hydroxide. Workup identical to that in Example 4 will furnish the desired solid support.

EXAMPLE 6

Immobilization of Phosphoric Acid Mono-{2-[2-(5-mercapto-tetrazol-1-yl)-acetylamino]-ethyl}ester on Cellulose Beads The purpose of this example is to demonstrate the preparation of a solid substrate comprised of a heterocycle containing 4 N atoms and bearing a phosphate group indirectly linked to the heterocycle.

Phosphoric acid mono-{2-[2-(5-mercapto-tetrazol-1-yl)-acetylamino]-ethyl}ester can be obtained from the reaction between 5-mercapto-1-tetrazolacetic acid and O-phosphoethanolamine. The product can be linked to cellulose beads in a manner analogous to that of Example 1 using allyl bromide or Example 2 using allylglycidyl-ether.

EXAMPLE 7

Immobilization of 2-[2-(5-Mercapto-tetrazol-1-yl)-acetylamino]-ethanesulfonic Acid on Cellulose Beads The purpose of this example is to demonstrate the preparation of a solid substrate comprised of a heterocycle containing 4 N atoms and bearing a sulfonic acid group indirectly linked to the heterocycle.

2-[2-(5-Mercapto-tetrazol-1-yl)-acetylamino]-ethanesulfonic acid can be obtained from the reaction between 5-mercapto-1-tetrazolacetic acid and 2-aminoethane sulfonic acid. The product can be linked to cellulose beads in a manner analogous to that of Example 1 using allyl bromide or Example 2 using allylglycidyl-ether, In an alternate procedure, 5-mercapto-1-tetrazolacetic acid is first linked to beads using allyl bromide in a manner analogous to that of Example 1. Subsequently, 2-aminoethane sulfonic acid is condensed with the product by condensation of the 2-amino group to the carboxyl group of the tetrazole.

EXAMPLE 8

Separation of Antibodies from Bovine Serum

The purpose of this example is to demonstrate the isolation and purification of antibodies derived from serum using a solid substrate of this invention.

A column of 1.6 cm in diameter was packed with 10 ml of the solid substrate prepared according to Example 1. The solid substrate was equilibrated with a 50 mM acetate buffer at pH 5.5 and 0.14 M sodium chloride.

Next, the pH of a bovine serum sample was adjusted to pH 5.5, 2 ml of which was loaded directly onto the column. The column was washed extensively with the acetate buffer to ensure the elimination of non-adsorbed proteins. Bound impurities were removed by washing the column with phosphate buffered saline.

The desired antibodies were eluted by flushing the column with a 100 mM Tris-HCl buffer at pH 9.5. The collected fraction contained mostly antibodies of IgG class, the purity of which was estimated to be about 70-90%. This antibody fraction can be further purified by fractionation on another appropriate column.

EXAMPLE 9

Separation of Antibody from Milk Whey

The purpose of this example is to demonstrate the isolation and purification of antibodies derived from milk whey using a solid substrate of this invention.

A column identical to that described in Example 8 was loaded with 50 ml of milk whey. Milk whey already has a pH close to 5.5, and thus requires no adjustment of pH.

In a manner identical to that in Example 8, the column was washed, equilibrated, and flushed to collect the desired antibodies, the purity of which was estimated to be about 80-95%. This antibody fraction can be purified further by fractionation on another, appropriate column.

EXAMPLE 10

Preparation of an MBISA Biochip Array

SubstratePreparation

A flat aluminum substrate ("the chip") was coated via sputtering with Silicon Dioxide. A hydrophobic polymer (Cytonix, Beltsville, Md.) was applied to create addressable locations on the chip. Chips prepared in this manner were cleaned in a plasma cleaner and introduced into a chemical vapor deposition (CVD) oven. Methacryloxypropyl-trimethoxy silane was deposited via CVD onto the chips, a vacuum was applied, and the coated chips then cured at 60° C.

Dextran Modification

Allylation 10 g of Dextran (Sigma, MW ~75,000) was dissolved in 50 ml of deionized water, together with 100 mg of Sodium Borohydride to prevent oxidation. Sodium hydroxide solution (12.5 ml) was added to the dextran mixture, followed after 5 minutes by the addition of of allylbromide (3 mL). After 16 hrs with stirring, the product (allyl-dextran) was precipitated by the addition of 100 mL of acetone. The allylated dextrose was purified by twice precipitating the crude product from water solutions (50 mL) by the addition of acetone (100 mL). Finally, the purified product was redissolved in 200 ml of DI water, then freeze dried.

Bromination and Mercaptobenzimidazole Sulfonic Acid Modification

A water solution (100 mL) of allylated dextran (5 g) was treated sequentially with 1.5 g of N-Bromosuccinimide (Aldrich) and 2.5 g of Potassium Bromide. Then the pH was adjusted between 3.7 and 3.9 with Phosphoric Acid (diluted ⅓ with DI water). The resultant solution was stirred for one hour at room temperature (under a fume hood because of bromine generation).

2.7 of mercaptobenzimidazole sulfonic acid (Aldrich) was added to the solution. The pH was adjusted between 11 and 11.5 with 10M NaOH (aq), checked for one hour, and adjusted if necessary. After 16 hrs, 200 mL of acetone were added to the solution to precipitate the crude product, which was subsequently redissolved in 100 mL of water, then dialysed with MWCO 5,000 Cellulose Dialysis bag. The resultant product (MBI-dextran) was obtained as a white powder after freeze drying.

Benzophenone Dextran

In a 250 ml round bottom flask were added 2.26 g of 4-benzoylbenzoic acid (Aldrich, Benzophenone 4-carboxylic acid), 2.26 g of Dicyclohexylcarbodiimide (Aldrich, DCC) and 50 mL of dry DMSO.

A solution of 8.1 g of Dextran (Sigma, MW ~75,000) and 0.12 g of dimethylaminopyridine (DMAP) in 100 ml of DMSO was added dropwise to the stirred benzophenone solution through an addition funnel. After stirring 16 hr, the resultant precipitate was filtered, then the solvent from the filtrate was removed on a rotary evaporator. In some instances, the crude product can be further purified by recrystallization.

Coating of MBI Polymer onto the Substrate 1.35 g of MBI dextran and 0.15 g of Benzophenone dextran as prepared above were dissolved in 100 mL of DI water. 1 μl of this dextran solution and 1 μl of ethanol were deposited sequentially onto the silanated chip. The coated chip was dried in an oven and irradiated (near UV) for 20 min. to cure. Following the irradiation, the chip was washed with DI water and dried.

Although the present invention has been described and illustrated with respect to preferred embodiments and a preferred use thereof, it is not to be so limited since modifications and changes can be made therein which are within the full scope of the invention as set forth in the appended claims.

We claim:

1. A method for the separation of biological substances from a sample, comprising:
   (a) contacting a solid substrate comprising:
   a solid support;
   a polycyclic group comprising at least one aromatic group fused to a heterocyclic or heteroaromatic group, and that is substituted with a sulfate, sulfonate, phosphate, or phosphonate group;
   wherein the polycyclic group is linked to the solid support through a linking group and the linking group is represented by the formula

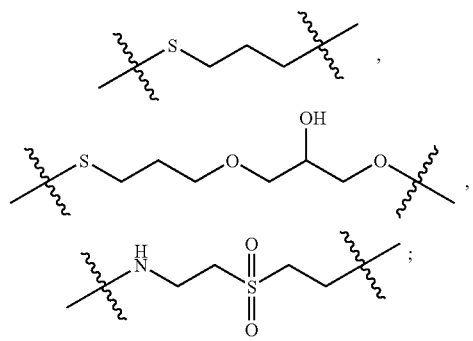

with a liquid sample that contains at least one biological substance;
   (b) adsorbing the biological substance to the solid substrate;
   (c) washing the solid substrate obtained in (b) with an equilibration buffer; and
   (d) adjusting the pH such that the biological substance desorbs from the solid substrate.

2. The method according to claim 1, further comprising adjusting the pH of the sample such that the biological substance adsorbs onto the solid substrate.

3. The method according to claim 2, wherein the pH in (b) is adjusted to a value between about 4 to about 6.

4. The method according to claim 1, wherein the pH in (d) is adjusted to a value between about 8 to about 11.

5. The method according to claim 2, wherein the pH in (b) is adjusted to a value between about 4 to about 6 and the pH in (d) is adjusted to a value between about 8 to about 11.

6. The method according to claim 1, wherein the separation is accomplished via fixed bed, fluidized bed, or batch chromatography.

7. The method according to claim 1, wherein the biological substance is selected from proteins, viruses, nucleic acids, carbohydrates, and lipids.

8. The method according to claim 7 wherein the biological substance is a protein.

9. The method according to claim 8 wherein the protein is selected from immunoglobulins, hormones, clotting factors, cytokines, peptides, and enzymes.

10. The method according to claim 9 wherein the protein is an immunoglobulin.

11. The method of claim 1, wherein the solid support is an organic material.

12. The method of claim 11, wherein the organic material is one selected from the group consisting of cellulose, agarose, dextran, polyacrylates, polystyrene, polyacrylamide, polymethacrylamide, copolymers of styrene and divinylbenzene, and mixtures thereof.

13. The method of claim 1, wherein the heterocyclic or heteroaromatic group comprises at least one S heteroatom.

14. The method of claim 1, wherein the heterocyclic or heteroaromatic group comprises at least one N heteroatom.

15. The method of claim 1, wherein the heterocyclic or heteroaromatic group comprises at least one S heteroatom and one N heteroatom.

16. The method of claim 1, wherein the aromatic group is phenyl, naphthyl, anthracenyl, phenanthrenyl, or acenaphthylenyl.

17. The method of claim 1, wherein the heterocyclic or heteroaromatic group is thiazoline, thiazolidone, imidazole, imidazoline, thiazole, triazoles, tetrazole, thiadiazole, pyridine, or morpholine.

18. The method of claim 1, wherein the polycyclic group is benzimidazole or benzothiazole.

19. The method of claim 1, wherein the heterocyclic or heteroaromatic group comprises at least one O heteroatom.

20. The method of claim 1, wherein the heterocyclic or heteroaromatic group comprises at least one O heteroatom and one N heteroatom.

* * * * *